(12) United States Patent
Gure et al.

(10) Patent No.: US 6,339,140 B1
(45) Date of Patent: Jan. 15, 2002

(54) SSX FAMILY PROTEINS

(75) Inventors: Ali O. Gure, New York, NY (US); Ozlem Tureci; Ugur Sahin, both of Homburg/Saar (DE); Solam Tsang; Matthew J. Scanlan, both of New York, NY (US); Alexander Knuth, Frankfurt am Main; Michael Pfreundschuh, Homburg/Saar, both of (DE); Lloyd J. Old; Yao-Tseng Chen, both of New York, NY (US)

(73) Assignees: Ludwig Institute for Cancer Research, New York; Cornell Medical Research Foundation, Ithaca; Memorial Sloan Kettering Cancer Center, New York, all of NY (US)

( * ) Notice: Subject to any disclaimer, the term of this patent is extended or adjusted under 35 U.S.C. 154(b) by 0 days.

(21) Appl. No.: 09/796,780

(22) Filed: Mar. 1, 2001

Related U.S. Application Data

(62) Division of application No. 08/851,138, filed on May 5, 1997, now Pat. No. 6,291,658.

(51) Int. Cl.[7] .......................... C07K 1/00; C07K 14/00; C07K 17/00; A01N 37/18; A01K 38/00
(52) U.S. Cl. ............................................ 530/350; 514/2
(58) Field of Search ............................ 530/350; 514/2; 536/23.1, 23.5; 435/320.1, 325

(56) References Cited

U.S. PATENT DOCUMENTS 5,888,751 A * 3/1999 Tureci ...................... 438/7.23

* cited by examiner

*Primary Examiner*—Anthony C. Caputa
*Assistant Examiner*—Jennifer Hunt
(74) *Attorney, Agent, or Firm*—Fulbright & Jaworski, LLP

(57) ABSTRACT

The invention relates to members of the SSX family of genes, as well as their uses.

4 Claims, No Drawings

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 576 nucleotides
      (B) TYPE: nucleic acid
      (C) STRANDEDNESS: single
      (D) TOPOLOGY: linear (xi) SEQUENCE DESCRIPTION: SEQ ID NO: 1:

```
ATGAACGGAG ACGACGCCTT TGCAAGGAGA CCCAGGGATG ATGCTCAAAT ATCAGAGAAG      60

TTACGAAAGG CCTTCGATGA TATTGCCAAA TACTTCTCTA AGAAAGAGTG GGAAAAGATG     120

AAATCCTCGG AGAAAATCGT CTATGTGTAT ATGAAGCTAA ACTATGAGGT CATGACTAAA     180

CTAGGTTTCA AGGTCACCCT CCCACCTTTC ATGCGTAGTA AACGGGCTGC AGACTTCCAC     240

GGGAATGATT TTGGTAACGA TCGAAACCAC AGGAATCAGG TTGAACGTCC TCAGATGACT     300
```

```
TTCGGCAGCC TCCAGAGAAT CTTCCCGAAG ATCATGCCCA AGAAGCCAGC AGAGGAAGAA      360

AATGGTTTGA AGGAAGTGCC AGAGGCATCT GGCCCACAAA ATGATGGGAA ACAGCTGTGC      420

CCCCCGGGAA ATCCAAGTAC CTTGGAGAAG ATTAACAAGA CATCTGGACC CAAAAGGGGG      480

AAACATGCCT GGACCCACAG ACTGCGTGAG AGAAAGCAGC TGGTGGTTTA TGAAGAGATC      540

AGCGACCCTG AGGAAGATGA CGAGTAACTC CCCTCG                                576

(2) INFORMATION FOR SEQ ID NO: 2:

(i) SEQUENCE CHARACTERISTICS:
        (A) LENGTH: 576 nucleotides
        (B) TYPE:   nucleic acid
        (C) STRANDEDNESS: single
        (D) TOPOLOGY:     linear (xi) SEQUENCE DESCRIPTION: SEQ ID NO: 2:

ATGAACGGAG ACGACGCCTT TGTACGGAGA CCTAGGGTTG GTTCTCAAAT ACCACAGAAG       60

ATGCAAAAGG CCTTCGATGA TATTGCCAAA TACTTCTCTG AGAAAGAGTG GGAAAAGATG      120

AAAGCCTCGG AGAAAATCAT CTATGTGTAT ATGAAGAGAA AGTATGAGGC CATGACTAAA      180

CTAGGTTTCA AGGCCACCCT CCCACCTTTC ATGCGTAATA AACGGGTCGC AGACTTCCAG      240

GGGAATGATT TTGATAATGA CCCTAACCGT GGGAATCAGG TTGAACATCC TCAGATGACT      300

TTCGGCAGGC TCCAGGGAAT CTTCCCGAAG ATCACGCCCG AGAAGCCAGC AGAGGAAGGA      360

AATGATTCAA AGGGAGTGCC AGAAGCATCT GGCCCACAGA ACAATGGGAA ACAGCTGCGC      420

CCCTCAGGAA AACTAAATAC CTCTGAGAAG GTTAACAAGA CATCTGGACC CAAAAGGGGG      480

AAACATGCCT GGACCCACAG AGTGCGTGAG AGAAAGCAAC TGGTGGATTA TGAAGAGATC      540

AGCGACCCTG CGGAAGATGA CGAGTAACTC CCCTCA                                576

(2) INFORMATION FOR SEQ ID NO: 3:

(i) SEQUENCE CHARACTERISTICS:
        (A) LENGTH:  23 nucleotides
        (B) TYPE:  nucleic acid
        (C) STRANDEDNESS: single
        (D) TOPOLOGY: linear (xi) SEQUENCE DESCRIPTION: SEQ ID NO: 3:

CACACAGGAT CCATGAACGG AGG                                               23

(2) INFORMATION FOR SEQ ID NO: 4:

(i) SEQUENCE CHARACTERISTICS:
        (A) LENGTH:  33 nucleotides
        (B) TYPE:  nucleic acid
        (C) STRANDEDNESS: single
        (D) TOPOLOGY: linear (xi) SEQUENCE DESCRIPTION: SEQ ID NO: 4:

CACACAAAGC TTTGAGGGGA GTTACTCGTC ATC                                    33

(2) INFORMATION FOR SEQ ID NO: 5:

(i) SEQUENCE CHARACTERISTICS:
        (A) LENGTH:  23 nucleotides
        (B) TYPE:  nucleic acid
        (C) STRANDEDNESS: single
        (D) TOPOLOGY: linear (xi) SEQUENCE DESCRIPTION: SEQ ID NO: 5:

CTAAAGCATC AGAGAAGAGA AGC                                               23
```

(2) INFORMATION FOR SEQ ID NO: 6:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 6:

AGATCTCTTA TTAATCTTCT CAGAAA                              26

(2) INFORMATION FOR SEQ ID NO: 7:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 7:

GTGCTCAAAT ACCAGAGAAG ATC                                 23

(2) INFORMATION FOR SEQ ID NO: 8:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 8:

TTTTGGGTCC AGATCTCTCG TG                                  22

(2) INFORMATION FOR SEQ ID NO: 9:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO: 9:

GGAAGAGTGG GAAAAGATGA AAGT                                24

(2) INFORMATION FOR SEQ ID NO: 10:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 10:

CCCCTTTTGG GTCCAGATAT CA                                  22

(2) INFORMATION FOR SEQ ID NO: 11:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 11:

AAATCGTCTA TGTGTATATG AAGCT                              25

(2) INFORMATION FOR SEQ ID NO: 12:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 12:

GGGTCGCTGA TCTCTTCATA AAC      23

(2) INFORMATION FOR SEQ ID NO: 13:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 13:

GTTCTCAAAT ACCACAGAAG ATG      23

(2) INFORMATION FOR SEQ ID NO: 14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 14:

CTCTGCTGGC TTCTCGGGCG      20

SSX FAMILY PROTEINS

RELATED APPLICATION

This application is a divisional of U.S. patent application Ser. No. 08/851,138, filed May 5, 1997, now U.S. Pat. No. 6,291,658.

FIELD OF THE INVENTION

This invention relates to the isolation and cloning of genes which are members of the "SSX" family, which is discussed herein, and the uses thereof.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by antitumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of cytotoxic T cell lines (CTLs) with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. patent applications Ser. No. 08/580,980, and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., sunra, as well as Crew, et al., EMBO J 144: 2333–2340 (1995).

The SEREX methodology has been applied to esophageal cancer samples, an esophageal cancer associated antigen has now been identified, and its encoding nucleic acid molecule isolated and cloned, as per U.S. patent application Ser. No. 08/725,182, now U.S. Pat. No. 5,804,381 filed Oct. 3, 1996, incorporated by reference herein.

The relationship between some of the tumor associated genes and a triad of genes, known as the SSX genes, is under investigation. See Sahin, et al., supra; Tureci, et al., Cancer Res 56:4766–4772 (1996). One of these SSX genes, referred to as SSX2, was identified, at first, as one of two genes involved in a chromosomal translocation event (t(X; 18) (p11.2; q 11.2)), which is present in 70% of synovial sarcomas. See Clark, et al., Nature Genetics 7:502–508 (1994); Crew et al., EMBO J 14:2333–2340 (1995). It was later found to be expressed in a number of tumor cells, and is now considered to be a tumor associated antigen referred to as HOM-MEL-40. See Tureci, et al, supra. Its expression to date has been observed in cancer cells, and normal testis only. This parallels other members of the "CT" family of tumor antigens, since they are expressed only in cancer and testis cells. Crew et al. also isolated and cloned the SSX1 gene, which has 89% nucleotide sequence homology with SSX2. See Crew et al., supra. Additional work directed to the identification of SSX genes has resulted in the identification of SSX3, as is described by DeLeeuw, et al., Cytogenet. Genet 73:179–183 (1996). The fact that SSX presentation parallels other, CT antigens suggested to the inventors that other SSX genes might be isolated.

Application of a modification of the SEREX technology described supra has been used, together with other techniques, to clone two, additional SSX genes, referred to as SSX4 and SSX5 hereafter as well as an alternate splice variant of the SSX4 gene. Specifically, while the SEREX methodology utilizes autologous serum, the methods set forth infra use allogenic serum. This, as well as other features of the invention, are set forth in the disclosure which follows.

DETAILED DESCRIPTION OF PREFERRED EMBODIMENTS

EXAMPLE 1

A human testicular cDNA expression library was obtained, and screened, with serum from a melanoma patient identified as MZ2. See e.g., parent application U.S. patent application Ser. No. 08/479,328, now U.S. Pat. No. 5,698,396 incorporated by reference; also see U.S. patent application Ser. No. 08/725,182 now U.S. Pat. No. 5,804,381 also incorporated by reference; Sahin, et al., Proc. Natl. Acad. Sci. USA 92:11810–11813 (1995). This serum had been treated using the methodology described in these references. Briefly, serum was diluted 1:10, and then preabsorbed with transfected E. coli lysate. Following this preabsorption step, the absorbed serum was diluted 1:10, for a final dilution of 1:100. Following the formal dilution the samples were incubated overnight at room temperature, with nitrocellulose membranes containing phage plaques prepared using the methodology referred to supra. The nitrocellulose membranes were washed, incubated with alkaline phosphatase conjugated goat anti-human $Fc_\gamma$ secondary antibodies, and the reaction was observed with the substrates 5-bromo-4-chloro-3-indolyl phosphate and nitroblue tetrazolium. In a secondary screen, any phagemids which encoded human immunoglobulin were eliminated.

A total of $3.6 \times 10^5$ pfus were screened, resulting in eight positive clones. Standard sequencing reactions were carried out, and the sequences were compared to sequence banks of known sequences.

Of the eight clones, two were found to code for known autoimmune disease associated molecules, i.e., Golgin-95 (Fritzler, et al., J. Exp. Med.178:49–62 (1993)), and human upstream binding factor (Chan, et al., J. Exp. Med. 174:1239–1244 (1991)). Three other clones were found to encode for proteins which are widely expressed in human tissue, i.e., ribosomal receptor, collagen type VI globular domain, and rapamycin binding protein. Of the remaining three sequences, one was found to be non-homologous to any known sequence, but was expressed ubiquitously in human tissues (this was found via RT-PCR analysis, but details are not provided herein). The remaining two were found to be identical to full length HOM-MEL-40, described in 08/479,328, while the eighth clone was found to be almost identical to "SSX3," as described by DeLeeuw, et al., Cytogenet. Cell Genet 73:179–183 (1996), differing therefrom in only two base pair differences in the coding region. These differences are probably artifactual in nature; however, the clone also included a 43 base pair 3'-untranslated region.

EXAMPLE 2

In order to carry out Southern blotting experiments, described infra, the SSX genes were amplified, using RT-PCR.

To do this, two primers were prepared using the published SSX2 sequence i.e., MEL-40A:

5'- CACACAGGAT CCATGAACGG AGA (SEQ ID NO: 3), and MEL-40B:

5'- CACACAAAGC TTTGAGGGGA GTTACTCGTC ATC (SEQ. ID NO: 4)

See Crew, et al., EMBO J 14:2333–2340 (1995). Amplification was then carried out using 0.25 U Taq polymerase in a 25 μl reaction volume, using an annealing temperature of 60° C. A total of 35 cycles were carried out.

EXAMPLE 3

The RT-PCR methodology described supra was carried out on testicular total RNA, and the amplification product was used in Southern blotting experiments.

Genomic DNA was extracted from non-neoplastic tissue samples, and then subjected to restriction enzyme digestion, using BamHI, Eco RI, or HindIII in separate experiments and then separated on a 0.7% agarose gel, followed by blotting on to nitrocellulose filters. The amplification products described supra were labeled with $^{32}P$, using well-known methods, and the labeled materials were then used as probes under high stringency conditions (65° C., aqueous buffer), followed by high stringency washes, ending with a final wash at 0.2×SSC, 0.2% SDS, 65° C.

The Southern blotting revealed more than 10 bands, in each case (i.e., each of the BamHI, EcoRI, and HindIII digests), strongly suggesting that there is a family of SSX genes which contained more than the three identified previously. In view of this observation, an approach was designed which combined both PCR cloning, and restriction map analysis, to identify other SSX genes.

EXAMPLE 4

When the sequences of SSX1, 2 and 3 were compared, it was found that they shared highly conserved 5' and 3' regions, which explained why the olignucleotides of SEQ ID NOS: 3 and 4 were capable of amplifying all three sequences under the recited conditions, and suggested that this homology was shared by the family of SSX genes, whatever its size. Hence, the oligonucleotides of SEQ ID NOS: 3 and 4 would be sufficient to amplify the other members of the SSX gene family.

An analysis of the sequences of SSX1, 2 and 3 revealed that SSX1 and 2 contained a BglII site which was not shared by SSX3. Similarly, SSX3 contained an EcoRV site not shared by the other genes.

In view of this information, testicular cDNA was amplified, using SEQ ID NOS: 3 and 4, as described supra, and was then subjected to BglII digestion. Any BglII resistant sequences were then cloned, sequenced, and compared with the known sequences.

This resulted in the identification of two previously unidentified sequences, referred to hereafter as SSX4 and SSX5, presented as SEQ ID NOS: 1 and 2 herein. A search of the GenBank database found two clones, identified by Accession Number N24445 and W00507, both of which consisted of a sequence-tag-derived cDNA segments. The clone identified by N24445 contained the 3'-untranslated region of SSX4, and part of its coding sequence, while the one identified, as W00507 contained a shorter fragment of the 3'-untranslated region of SSX4, and a longer part of the coding sequence. Specifically, N24445 consists of base 344 of SSX4 (SEQ ID NO:1), through the 3-end, plus 319 bases 3' of the stop codon. The W00507 sequence consists of a 99 base pair sequence, showing no homology to SSX genes followed by a region identical to nucleotides 280 through the end of SEQ ID NO: 1, through 67 bases 3' of the stop codon of SEQ ID NO: 1.

Two forms of SSX4 (SEQ ID NO: 1) were identified. One of these lacked nucleotides 331 to 466 but was otherwise identical to SSX4 as presented in SEQ ID NO: 1. As is described infra, the shorter form is an alternatively spliced variant.

In Table 1, which follows, the nucleotide and amino acid sequences of the 5 known members of the SSX family are compared. One reads the table horizontally for nucleotide homology, and vertically for amino acid homology.

Table 1 Nucleotide and amino acid homology among SSX family members

TABLE 1

Nucleotide and amino acid homology among SSX family members

| | Nucleotide Sequence Homology (%) | | | | |
|---|---|---|---|---|---|
| | SSX1 | SSX2 | SSX3 | SSX4 | SSX5 |
| SSX1 | | 89.1 | 89.6 | 89.4 | 88.7 |
| SSX2 | 78.2 | | 95.1 | 91.5 | 92.9 |
| SSX3 | 77.7 | 91.0 | | 91.1 | 92.7 |
| SSX4 | 79.3 | 79.8 | 80.9 | | 89.8 |
| SSX5 | 76.6 | 83.5 | 84.0 | 77.7 | |
| | Amino Acid Sequence Homology (%) | | | | |

Hence, SSX1 and SSX4 share 89.4% homology on the nucleotide level, and 79.3% homology on the amino acid level.

When the truncated form of SSX4 is analyzed, it has an amino acid sequence completely different from others, due to alternate splicing and shifting of a downstream open reading frame. The putative protein is 153 amino acids long, and the 42 carboxy terminal amino acids show no homology to the other SSX proteins.

EXAMPLE 5

The genomic organization of the SSX2 genes was then studied. To do this, a genomic human placental library (in lambda phage) was screened, using the same protocol and probes described supra in the discussion of the southern blotting work. Any positive primary clones were purified, via two additional rounds of cloning.

Multiple positive clones were isolated, one of which was partially sequenced, and identified as the genomic clone of SSX2. A series of experiments carrying out standard subcloning and sequencing work followed, so as to define the exon-intron boundaries.

The analysis revealed that the SSX2, gene contains six exons, and spans at least 8 kilobases. All defined boundaries were found to observe the consensus sequence of exon/intron junctions, i.e. GT/AG.

The alternate splice variant of SSX4, discussed supra, was found to lack the fifth exon in the coding region. This was ascertained by comparing it to the SSX2 genomic clone, and drawing correlations therefrom.

EXAMPLE 6

The expression of individual SSX genes in normal and tumor tissues was then examined. This required the construction of specific primers, based upon the known sequences, and these follow, as SEQ ID NOS: 5–14:

TABLE 2

Gene-specific PCR primer sequences for individual SSX genes

| | | |
|---|---|---|
| SSX 1A (5'): | 5'-CTAAAGCATCAGAGAAGAGAAGC | [nt.44-66] |
| SSX 1B (3'): | 5'-AGATCTCTTATTAATCTTCTCAGAAA | [nt.440-65] |
| SSX 2A (5'): | 5'-GTGCTCAAATACCAGAGAAGATC | [nt.41-63] |
| SSX 2B (3'): | 5'-TTTTGGGTCCAGATCTCTCGTG | [nt.102-25] |
| SSX 3A (5'): | 5'-GGAAGAGTGGGAAAAGATGAAAGT | [nt.454-75] |
| SSX 3B (3'): | 5'-CCCCTTTTGGGTCCAGATATCA | [nt.458-79] |
| SSX 4A (5'): | 5'-AAATCGTCTATGTGTATATGAAGCT | [nt.133-58] |
| SSX 4B (3'): | 5'-GGGTCGCTGATCTCTTCATAAAC | [nt.526-48] |
| SSX 5A (5'): | 5'-GTTCTCAAATACCACAGAAGATG | [nt.39-63] |
| SSX 5B (3'): | 5'-CTCTGCTGGCTTCTCGGGCG | [nt.335-54] |

The specificity of the clones was confirmed by amplifying the previously identified cDNA for SSX1 through SSX5. Taq polymerase was used, at 60° C. for SSX1 and 4, and 65° C. for SSX2, 3 and 5. Each set of primer pairs was found to be specific, except that the SSX2 primers were found to amplify minute (less than 1/20 of SSX2) amounts of SSX3 plasmid DNA.

Once the specificity was confirmed, the primers were used to analyze testicular mRNA, using the RT-PCR protocols set forth supra.

The expected PCR products were found in all 5 cases, and amplification with the SSX4 pair did result in two amplification products, which is consistent with alternative splice variants.

The expression of SSX genes in cultured melanocytes was then studied. RT-PCR was carried out, using the protocols set forth supra. No PCR product was found. Reamplification resulted in a small amount of SSX4 product, including both alternate forms, indicating that SSX4 expression in cultured melanocytes is inconsistent and is at very low levels when it occurs.

This analysis was then extended to a panel of twelve melanoma cell lines. These results are set forth in the following table.

Table 3 SSX expression in melanoma cell lines detected by RT-PCR*

TABLE 3

SSX expression in melanoma cell lines detected by RT-PCR*

| | SSX1 | SSX2 | SSX3 | SSX4 | SSX5 |
|---|---|---|---|---|---|
| MZ2-Mel 2.2 | + | + | − | − | − |
| MZ2-Mel 3.1 | + | + | − | − | − |
| SK-MEL-13 | − | − | − | − | − |
| SK-MEL-19 | − | − | − | − | − |
| SK-MEL-23 | − | − | − | − | − |
| SK-MEL-29 | − | − | − | − | − |
| SK-MEL-30 | −* | −* | − | −* | − |
| SK-MEL-31 | − | − | − | − | − |
| SK-MEL-33 | − | − | − | − | − |
| SK-MEL-37 | + | + | − | + | + |
| SK-MEL-179 | − | − | − | − | − |
| M24-MET | − | − | − | − | − |

*Positive (+) denotes strong expression. Weak positivity was observed inconsistently in SK-MEL-30 for SSX 1,2, and 4, likely representing low level expression.

The foregoing examples describe the isolation and cloning of nucleic acid molecules for the SSX4, splice variant of SSX4, and SSX5 genes. As was indicated, supra, these genes are expressed in tumor cells, thereby enabling the skilled artisan to utilize these for, e.g., assaying for cancer, such as melanoma. As the genes express a protein which, in turn, would provoke generation of antibodies in vivo, these proteins are also a part of the invention as are the isolated antibodies specific for them.

The isolated nucleic acid molecules of the invention encompass those degenerate sequences which, though not identical to SEQ ID NO: 1, its splice variant, or SEQ ID NO: 2, do encode the same proteins which these sequences encode. Also a part of the invention are expression vectors which comprise these molecules, operably linked to a promoter, and the cell lines or cell strains which are transformed or transfected with these vectors, or the nucleic acid molecules themselves. These are all useful in making the protein, e.g., as well as for producing amplified copies of the relevant sequences.

Also, a part of the invention are those nucleic acid molecules defined herein by SEQ ID NOS: 5 through 14, compositions containing these, and the use thereof in assaying for expression of one or more SSX gene. Any nucleic acid hybridization methodology can be used, including, e.g., PCR methodologies. The antibodies of the invention may also be used in assays, but in this case the target is the expression product of the SSX genes.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated protein encoded by (i) an isolated nucleic acid molecule having the nucleotide sequence of SEQ ID NO:1, or (ii) an isolated nucleic acid molecule having the nucleotide sequence of SEQ ID NO: 2, or (iii) an isolated nucleic acid molecule having nucleotides 1–330 of SEQ ID NO:1 concatenated to nucleotides 467–576 of SEQ ID NO:1.

2. The isolated protein of claim 1, encoded by the nucleotide sequence of SEQ ID NO:1.

3. The isolated protein of claim 1, encoded by the nucleotide sequence of SEQ ID NO:2.

4. The isolated protein of claim 1 encoded by the nucleotide sequence having nucleotides 1–330 of SEQ ID NO:1 concatenated to nucleotides 467–576 of SEQ ID NO:1.

* * * * *